(12) United States Patent
Grint et al.

(10) Patent No.: US 6,544,504 B1
(45) Date of Patent: Apr. 8, 2003

(54) COMBINED USE OF INTERLEUKIN 10 AND METHOTREXATE FOR IMMUNO-MODULATORY THERAPY

(75) Inventors: Paul C. Grint, San Diego, CA (US); Satwant Narula, West Caldwell, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 09/602,949

(22) Filed: Jun. 26, 2000

Related U.S. Application Data
(60) Provisional application No. 60/146,022, filed on Jul. 28, 1999.

(51) Int. Cl.$^7$ .......................... A61K 38/20; A01N 43/54
(52) U.S. Cl. ...................... 424/85.2; 514/256; 514/186
(58) Field of Search .................. 424/85.2; 514/258, 514/186

(56) References Cited

U.S. PATENT DOCUMENTS

| | | | | |
|---|---|---|---|---|
| 5,292,731 A | * | 3/1994 | Love | ........................ 514/186 |
| 5,536,724 A | * | 7/1996 | DeGraw et al. | ............ 514/258 |
| 5,593,671 A | | 1/1997 | Kerwar et al. | |
| 5,753,218 A | | 5/1998 | Smith et al. | |

FOREIGN PATENT DOCUMENTS

| | | | |
|---|---|---|---|
| WO | 93/18783 | 9/1993 | .......... A61K/37/02 |
| WO | 98/05357 | 2/1998 | .......... A61K/39/395 |
| WO | 98/24477 | 6/1998 | .......... A61K/45/06 |

OTHER PUBLICATIONS

Opal et al. 1998. Clinical Infectious Diseases. , vol. 27: pp. 1497–1507. Intereleukin–10: potential benefits and possible Risks in Clinical infectious diseases.*

Kalden et al. 1997. Current Opinion in Rheumatlogy. vol. 9: pp. 206–212. Biologic agents in the treament of inflammatory rheumatic diseases.* van Roon et al. Arthritis rheum 1996, May 36(5):829–35. Prevention and reversal of cartilage degradation in rheumatoid arthritis by interleukin–10 and interleukin–4.*

Isomaki p et al. Arthritis rhem 1996, Mar 39(3):386–95. Interleukin–10 functions as an antiinflammtory cytokine in rheumatois synovium.*

Tremaine, W.J., "The Medical Treatment of Active Crohn's Disease", *Drugs of Today 35* (Suppl. A):89–96 (1999).

Durez, P. et al., "Methotrexate inhibits LPS–induced tumor necrosis factor production in vivo", *Eur. Cytokine Netw.*, 9:669 (Dec. 1998).

Lacki, J. et al., "Circulating interleukin 10 and interleukin–6 serum levels in rheumatoid arthritis patients treated with methotrexate or gold salts: Preliminary report", *Inflamm. Res* 44:24 (1995).

Asadullah, K. et al., "IL–10 Is aKey Cytokine in Psoriasis. Proof of Principle by IL–10 Therapy: A New Therapeutic Approach", *J. Clin. Invest*, 101:783 (Feb. 1998).

Kremer, J. et al., "Clinical, Laboratory, Radiographic, and Histopathologic Features of Methotrexate–Associated Lung Injury In Patients with Rheumatoid Arthritis", *Arthritis & Rheumatism*, 40:1829 (Oct. 1997).

Opal, S.M. et al., "Interleukin–10: Potential Benefits and Possible Risks in Clinical Infectious Diseases", *Clinical Infectious Diseases* 27:1497, XP000915244 (1998).

Moritani M. et al., "Prevention of Adoptively Transferred Diabetes in Nonbese Diabetic Mice with IL–10–Transduced Islet–specific Th 1 Lymphocytes" *J. Clin. Invest.*, 98:1851, XP–002152055 (1996).

Weinblatt, M. et al., "rHUIL–10 (TENOVIL) plus Methotrexate (MTX) in active rheumatoid arthritis (RA): A phase I/II Study", *Arthritis & Rheumatism* 42:S170, XP000979189 (1999).

International Search Report for International Application No. PCT/US 00/20304 dated Jan. 30, 2001, from European Patent Office.

* cited by examiner

*Primary Examiner*—Gary Kunz
*Assistant Examiner*—Fozia Hamud

(57) ABSTRACT

A combination of interleukin 10 and methotrexate is used to suppress autoimmune diseases including arthritis and psoriasis. It has been discovered that administration of a combination of interleukin 10 and methotrexate causes suppression of T cell proliferation. Concurrent use of both agents avoids the toxicity associated with higher doses of methotrexate.

6 Claims, No Drawings

COMBINED USE OF INTERLEUKIN 10 AND METHOTREXATE FOR IMMUNO-MODULATORY THERAPY

CROSS-REFERENCE TO RELATED APPLICATIONS

This application is a non-provisional application that claims the priority of provisional application U.S. Ser. No. 60/146,022, filed Jul. 28, 1999. The Applicants' claim the benefits of this application under 35 U.S.C. §119(e).

FIELD OF THE INVENTION

The invention relates to a method for controlling autoimmune diseases, such as rheumatoid arthritis, inflammatory bowel disease, multiple sclerosis and psoriasis. In particular, the invention relates to the combined use of interleukin-10 and methotrexate for immuno-modulatory therapy.

BACKGROUND OF THE INVENTION

Interleukin 10 (IL-10), a cytokine produced by *T lymphocytes*, was first identified by its ability to inhibit interferon gamma (IFN-γ) and IL-2 synthesis by mouse and human *T lymphocytes* [Fiorentino et al., 1989, *J. Exp. Med.* 170:2081–2089; Moore et al., 1990, *Science* 248:1230–1252; Vieira et al., 1991, *Proc. Natl. Acad. Sci. USA* 88:1172–1177]. IL-10 was subsequently shown to be produced by B cells [O'Garra et al., 1990, *Internat. Immunol.* 2:821–828] and macrophages [Fiorentino et al., 1991, *J. Immunol.* 147:3815–3822].

IL-10 exerts a wide range of effects on a variety of cell types. IL-10 inhibits the synthesis of a wide spectrum of cytokines produced by T cells and monocytes. In addition to inhibiting the synthesis of IFN-γ and IL-2, IL-10 has also been shown to inhibit production of the monokines IL-1α, IL-1β, IL-6 and TNFα [de Waal et al., 1991, *J. Exp. Med.* 174:1209–1217]. IL-10 has growth promoting effects on murine thymocytes and T cells [MacNeil et al., 1990, *Immunol.* 145:4167] and mast cells [Thompson-Snipes et al., 1991, *J. Exp. Med.* 173:507–512], and it stimulates cytotoxic T-cell development [Chen and Zlotnik, 1991, *J. Immunol.* 147:528–533].

Mouse and human IL-10 have high sequence similarity with a protein encoded by an open reading frame in the Epstein-Barr Virus. The expression product of this open reading frame, named viral IL-10, also has the capacity to inhibit cytokine synthesis [Moore et al., 1990, *Science* 248:1230–1252; Vieira etal., 1991, *Proc. Natl. Acad. Sci. USA* 88:1172–1177].

Several cytokines, including IL-2, IFN-γ and TNF-α, have been shown to regulate the mixed lymphocyte reaction (MLR) [Shevach, 1985, *Annu. Rev. Immunol.* 3:397; Fidelus et al., 1982, *Transplantation* 34:308; Tadmori et al., 1985, *J. Immunol.* 134:4542–4550; Tadmori et al, 1986, *J. Immunol.* 136:1155–1162; Novelli et al., 1991, 147:1445–1450; Landolfo et al., 1985, *Science* 229:176–180; Shalaby et al., 988, *J. Immunol.* 141:499–505]. It has been reported that IFN-γ may play an important role in MLR graft rejection [Novelli et al., 1991, *J. Immunol.* 147:1445–1450; Landolfo et al., 1985, *Science* 229:176–180]. Antibodies to IFN-γ or to TNF [Shalaby et al., 1988, *J. Immunol.* 141:499–505] have been shown to block MLR-induced proliferation. In these studies it was found that antibodies to IFN-γ suppressed the MLR in human systems as well as allograft reactivity in vitro and in vivo in the mouse.

Methotrexate is known as N-[4-[[(2,4-diamino-6-pteridinyl)methyl] methylamino]benzoyl]-L-glutamic acid. The following references describe the preparation of methotrexate [see Seeger et al., *J.Am.Chem.Soc.*, 1949, 71:1753]; the metabolism of methotrexate [see Freeman, *J.Pharmacol.Exp.Ther.* 1958, 122:154; and Henderson et al., *Cancer Res.* 1965, 25:1008, 1018]; the toxicity of methotrexate [Condit et al., *Cancer* 1960, 13:222–249]; the pharmacokinetic models of methotrexate [Bischoff, et al., *J.Pharm.Sci* 1970, 59:149]; the metabolism and pharmacokinetics of methotrexate [Evans, *Appl.Pharmacokinet.* 1980, 518–548]; the clinical pharmacology of methotrexate [Bertino, *Cancer Chemother*, 1981, 3: 359–375; Jolivet et al., *N.Engl.J.Med.*, 1983, 309: 1094–1104] and the clinical experience of methotrexate in rheumatoid arthritis [*J.Rheumatol.*, 1985, 12, Suppl, 12, 1–44].

Methotrexate inhibits dihydrofolic acid reductase. Folic acid must be reduced to tetrahydrofolic acid by this enzyme in the process of DNA synthesis, repair and cellular replication. Therefore, methotrexate interferes with cellular reproduction.

SUMMARY OF THE INVENTION

The present invention provides a method for treating autoimmune disease comprising administering an effective amount of interleukin-10 (IL-10) and methotrexate (MTX) to a patient afflicted with an autoimmune disease.

This invention also provides a method for treating rheumatoid arthritis comprising administering an effective amount of interleukin-10 and methotrexate to a patient experiencing arthritis. Other conditions treatable by the method of the present invention include but are not limited to psoriasis, inflammatory bowel disease and multiple sclerosis.

Pharmaceutical compositions comprising a combination of IL-10 and MTX are also provided by this invention.

DETAILED DESCRIPTION OF THE INVENTION

In order that the invention described herein may be more fully understood, the following detailed description is set forth. All references cited herein are hereby incorporated in their entirety by reference.

It has unexpectedly been discovered that the combined/concurrent administration of IL-10 and MTX, or IL-10 and a MTX analogue, causes an unexpectedly strong suppression of T cell proliferation. While the invention is discussed herein in terms of the combined use of IL-10 and MTX, it is to be understood that an analogue of MTX may also be combined with IL-10 to cause synergistic suppression of T cell proliferation, and that such combinations are contemplated for use in the practice of this invention.

The combination of IL-10 and MTX can be advantageously used in the suppression of pathology associated with T cell responses. For example, considering the diverse biological activities of IL-10, the concurrent use of IL-10 and MTX provides long term treatment of inflammatory bowel disease and such autoimmune diseases as rheumatoid arthritis. The invention may also be used to treat autoimmune diseases such as diabetes mellitus, multiple sclerosis and myasthenia gravis; and to treat other diseases where MTX has been used, such as psoriasis.

Due to the activity of IL-10, MTX can be used in lower amounts, thereby avoiding or reducing the serious side effects normally associated with the use of this drug. The MTX/IL-10 combination therapy of the present invention is useful in treating patients who are non-responsive to MTX treatment alone. MTX/IL-10 therapy is also useful in patients who have developed a resistance to MTX due to its long-term use.

The methods of the invention can be used prophylactically or for treatment of established autoimmune disease. Individuals suitable for treatment by the methods of the invention include any individual at risk (predisposed) for developing rheumatoid arthritis, or an individual exhibiting clinical symptoms. Prophylactic use encompasses administration prior to onset of clinical symptoms of arthritis, to prevent or postpone onset of disease.

In the practice of the invention, IL-10 and-MTX are to be "concurrently" administered to a patient. Concurrently administering means the IL-10 and MTX are administered to the subject either (a) simultaneously in time (optionally by formulating the two together in a common carrier), or (b) at different times during the course of a common treatment schedule. In the latter case, the two compounds are administered sufficiently close in time to achieve the intended effect. The active agents may be administered together in a single pharmaceutical composition or separately. Both active agents (i.e., IL-10 and MTX) should be present in the patient at sufficient combined levels to be therapeutically effective. The routes of administration of the IL-10 and MTX may be the same or different. For any route of administration, single or divided doses may be used.

Generally, IL-10 and MTX are administered as a pharmaceutical composition comprising an effective amount of IL-10 and MTX in a pharmaceutical carrier. A pharmaceutical carrier can be any compatible, non-toxic substance suitable for delivering the compositions of the invention to a patient.

As used herein, "interleukin 10" or "IL-10" is defined as a protein which (a) has an amino acid sequence substantially identical to a known sequence of mature (i.e., lacking a secretory leader sequence) IL-10 as disclosed in International Application Publication No. 91/003249, and (b) has biological activity that is common to native IL-10. For the purposes of this invention, both glycosylated (e.g., produced in eukaryotic cells such as yeast or CHO cells) and unglycosylated (e.g., chemically synthesized or produced in *E. Coli*) IL-10 are equivalent and can be used interchangeably. Also included are muteins and other analogs, including viral IL-10, which retain the biological activity of IL-10.

IL-10 suitable for use in the invention can be obtained from a number of sources. For example, it can be isolated from culture media of activated T-cells capable of secreting the protein. Additionally, the IL-10 or active fragments thereof can be chemically synthesized using standard techniques known in the art. See, e.g., Merrifield, 1986, *Science* 233:341–347 and Atherton et al., *Solid Phase Peptide Synthesis, A Practical Approach*, 1989, IRL Press, Oxford.

Preferably, the protein or polypeptide is obtained by recombinant techniques using isolated nucleic acids encoding the IL-10 polypeptide. General methods of molecular biology are described, e.g., by Sambrook et al., 1989, *Molecular Cloning, A Laboratory Manual*, 2d Ed., Cold Spring Harbor, N.Y. and Ausubel et al. (eds). *Current Protocols in Molecular Biology*, Green/Wiley, New York (1987 and periodic supplements). The appropriate sequences can be obtained using standard techniques from either genomic or cDNA libraries. DNA constructs encoding IL-10 may also be prepared synthetically by established standard methods, e.g., in an automatic DNA synthesizer, and then purified, annealed, ligated and cloned in suitable vectors. Atherton et al., 1989. Polymerase chain reaction (PCR) techniques can be used. See e.g., *PCR Protocols: A Guide to Methods and Applications*, 1990, Innis et al, (ed.), Academic Press, New York.

The DNA constructs may contain the entire native sequence of IL-10 or a homologue thereof. The term "homologue" is intended to indicate a natural variant of the DNA sequence encoding IL-10 or a variant or fragment produced by modification of the DNA sequence. Examples of suitable modifications of the DNA sequence are nucleotide substitutions which do not give rise to another amino acid sequence or nucleotide substitutions which do give rise to a different amino acid sequence and therefore, possibly, a different protein structure. Other examples of possible modifications are insertions of one or several nucleotides into the sequence, addition of one or several nucleotides at either end of the sequence, or deletion of one or several nucleotides at either end or within the sequence. Any homologous DNA sequence encoding a protein which exhibits IL-10 activity (e.g., with respect to suppression of T cell proliferation) similar to that of the naive protein is contemplated for use in the claimed invention.

The nucleotide sequences used to transfect the host cells can be modified, as described above, to yield IL-10 muteins and fragments with a variety of desired properties. Such modified IL-10 can vary from the naturally-occurring sequence at the primary level, e.g., by amino acid insertions, substitutions, deletions and fusions. Preferably, amino acid substitutions will be conservative; i.e., basic amino acid residues will be replaced with other basic amino acid residues, etc. These modifications can be used in a number of combinations to produce the final modified protein chain.

Amino acid sequence variants can be prepared with various objectives in mind, including increasing serum half-life, facilitating purification or preparation, improving therapeutic efficacy, and lessening the severity or occurrence of side effects during therapeutic use. The amino acid sequence variants are usually predetermined variants not found in nature, although others may be post-translational variants, e.g., glycosylation variants or proteins which are conjugated to polyethylene glycol (PEG), etc. Such variants can be used in this invention as long as they retain the biological activity of IL-10.

Preferably, human IL-10 is used for the treatment of humans, although viral or mouse IL-10, or IL-10 from some other mammalian species, could be used instead. Most preferably, the IL-10 used is recombinant human IL-10. Recombinant production of human IL-10 is described in U.S. Pat. No. 5,231,012. Preparation of human and mouse IL-10 has been described in International Application Publication No. WO 91/00349. The cloning and expression of viral IL-10 (BCRFI protein) from Epstein Barr virus has been disclosed by Moore et al. [*Science* 248:1230, 1990], and is described in EP 0 506 836.

Administration of IL-10 is preferably parenteral by intraperitoneal intravenous, subcutaneous or intramuscular injection or infusion or by any other acceptable systemic method. Administration by intramuscular or subcutaneous injection is most preferred. Alternatively, the IL-10 may be administered by an implantable or injectable drug delivery system. See, e.g., Urquhart et al, 1984, *Ann Rev. Pharmacol. Toxicol* 24:199; Lewis, ed., 1981, *Controlled Release of Pesticides and Pharmaceuticals*, Plenum Press, New York, N.Y.: U.S. Pat. Nos. 3,773,919, and 3,270,960. Oral administration may also be carried out, using well known formulations which protect the IL-10 from gastrointestinal proteases.

Compositions useful for parenteral administration of such drugs are well known. See, e.g., Remington's Pharmaceutical Science, 11th Ed., 1990, Mack Publishing Co., Easton, Pa. When administered parenterally, the IL-10 is typically formulated in a unit dosage injectable form (solution, suspension, emulsion) in association with a pharmaceutical carrier. Examples of such carriers are normal saline, Ringer's solution, dextrose solution, and Hank's solution. Non-aqueous carriers such as fixed oils and ethyl oleate may also be used. A preferred carrier is 5% dextrose/saline. The carrier may contain minor amounts of additives such as substances that enhance isotonicity and chemical stability, e.g., buffers and preservatives. The IL-10 is preferably formulated in purified form substantially free of aggregates and other source proteins at a concentration in the range of about 100–2000 mg/ml. Any of the well known carrier proteins such as human serum albumin can also be added if desired.

IL-10 can also be delivered by standard gene therapy techniques, including e.g., direct DNA injection into tissues, the use of recombinant viral vectors or phospholipid and implantation of transfected cells. See, e.g., Rosenberg, 1992, J. Clin. Oncol. 10:180.

MTX may be administered in a manner as is conventionally practiced. See, e.g., Goodman and Gilman's The Pharmacological Basis of Therapeutics, 7th Ed, 1985, p. 1299. For example, methotrexate may be orally administered with an inert diluent or with an assimilable edible carrier, or it may be enclosed in hard or soft shell gelatin capsules, or it may be compressed into tablets, or it may be incorporated directly with the food of the diet. For oral therapeutic administration, methotrexate may be incorporated with excipients and used in the form of ingestible tablets, buccal tablets, troches, capsules, elixers, suspension, syrups, wafer, and the like. Such compositions and preparations should contain at least 0.5% of methotrexate. The percentage of the compositions and preparations may, of course, be varied and may conveniently be between about 2 to 60% of the weight of the unit. The amount of methotrexate in such therapeutically useful compositions is such that a suitable dosage will be obtained. Preferred compositions or preparations according to the present invention are prepared so that an oral dosage unit form contains between 0.025 and 35 mg of methotrexate.

The tablets, troches, pills, capsules and the like may also contain the following: a binder, such as gum tragacanth, acacia, corn starch or gelatin; excipients such as dicalciumphosphate; a disintegrating agent such as corn starch, alginic acid and the like; a lubricant such as magnesium stearate; and a sweetening agent such as sucrose, lactose or saccharin may be added or a flavoring agent such as peppermint, oil of wintergreen or cherry flavoring. When the dosage unit form is a capsule, it may contain, in addition to material of the above type, a liquid carrier. Various other materials may be present as coating or to otherwise modify the physical form of the dosage unit. For instance, tablets, pills, or capsules may be coated with shellac, sugar or both. A syrup or elixer may contain methotrexate, sucrose as a sweetening agent, methyl and propylparabens as preservative, a dye and flavoring such as cherry or an orange flavor. Of course, any material used in preparing any dosage unit form should be pharmaceutically pure and substantially non-toxic in the amounts employed. In addition, methotrexate may be incorporated into sustained-release preparations and formulations.

Methotrexate may also be administered parenterally or intraperitoneally. Solutions of methotrexate can be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases, the form must be sterile and must be fluid to the extent that easy syringability exists. The form must be stable under the conditions of manufacture and storage and must be preserved against the contamination action of microorganisms such as bacteria and fungi. The carrier can be a solvent or dispersion medium containing, for example, water, ethyl alcohol, polyol (for example, glycerol, propylene glycol, and liquid polyethylene glycol and the like), suitable mixtures thereof, and vegetable oils. The proper fluidity can be maintained, for example, by the use of a coating such as lecithin, by the maintenance of the required particle size in the case of dispersion and the use of surfactants. The prevention of the action of microorganisms can be brought about by various antibacterial and antifungal agents, for example, parabens, chlorobutanol, phenol, sorbic acid, thimerosal and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating methotrexate in the required amount in the appropriate solvent with various of the other ingredients enumerated above, as required, followed by filtered sterilization. Generally, dispersions are prepared by incorporating methotrexate into a sterile vehicle which contains the basic dispersion medium and the required other ingredients from those enumerated above. In the case of sterile powder, for the preparation of sterile injectable solutions, the preferred methods of preparation are vacuum drying and the freeze-drying technique which yield a powder of methotrexate, plus any additional desired ingredient from a previously sterile filtered solution thereof.

As used herein, "pharmaceutically acceptable carriers" includes any and all solvents, dispersion media, coating, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

It is especially advantageous to formulate parenteral compositions in dosage unit form for case of administration and uniformity of dosage. Dosage unit form as used herein refers to physically discrete units suited as unitary dosages for the mammalian subjects to be treated; each unit containing a predetermined quantity of active material calculated to produce the desired therapeutic effect in association with the required pharmaceutical carrier.

Methotrexate is compounded for convenient and effective administration in effective amounts with a suitable pharmaceutically acceptable carrier in dosage unit form as hereintofore disclosed. A unit dosage form can, for example, contain methotrexate in amounts ranging from about 0.1 to 400 mg, with from 1 to 35 mg being preferred, and 10 to 25 being most preferred. Expressed in proportions, methotrexate is generally present in from about 0.1 to about 40 mg/ml of carrier. In the case of compositions containing supplementary active ingredients, the dosages are determined by reference to the usual dose and manner of administration of said ingredients.

A single intravenous dosage, slow constant infusion, or repeated daily dosages can be administered. Daily dosages up to about 1 to 10 days are often sufficient. It is also possible to dispense one daily dosage or multiple daily doses or one dose on alternate or less frequent days. As can be seen from the dosage regimens, the amount of methotrexate administered is to be sufficient to relieve the autoimmune disease symptoms prevalent in diseases such as arthritis and psoriasis.

IL-10 and MTX are concurrently administered to a human patient in an amount effective to provide an immunosuppressive effect. As used herein "effective amount" means an amount sufficient to reduce or prevent rheumatoid arthritis, an autoimmune disease or psoriasis, and refers to the combined effects of the two agents working in concert. One or both agents may, for example, be used at a dose which, if used alone, would be considered suboptimal for the intended purpose.

Based on the judgment of the clinician, the amount of IL-10 and/or MTX will, of course vary. The effective amount for a particular patient will depend on such factors as the overall health and age of the patient, the route of administration, the severity of observed side-effects, and the like. The effective dose of IL-10 typically will range from about 0.1–100 $\mu$g/kg/day, preferably about 1–20 $\mu$g/kg/day in a single or divided doses. More preferably, the effective dose of IL-10 will be 8 $\mu$g/kg three times a week [TIW], 8 $\mu$g/kg daily or 20 $\mu$g/kg TIW. The effective dose of MTX typically range from about 1–100 mg/week, more preferably from about 5–35 mg/week, and most preferably from about 10–25 mg/week. The length of administration may vary and, in some cases, may continue over the remaining lifetime of a patient, to control autoimmune symptoms or graft rejection processes.

EXAMPLE 1

Safety and Tolerance Study of IL-10 in Combination with a Stable Dosing Reqimen of MTX in Patients with Active Rheumatoid Arthritis A multinational, multicenter, sequentially randomized, double-blind, placebo-controlled, rising multiple-dose study of IL-10 plus methotrexate (MTX) treatment was completed in patients with active rheumatoid arthritis.

Fifty patients were to receive one of five dosing regimens of IL-10 (SC) (1 $\mu$g/kg daily, 4 $\mu$g/kg daily, 8 $\mu$g/kg three times a week [TIW], 8 $\mu$g/kg daily and 20 $\mu$g/kg TIW) or placebo for 28 days, in addition to stable dosing with MTX (Treatment Phase). The patients were followed for 8 weeks after the end of IL-10 dosing (Follow-up Phase). Patients received MTX at therapeutic doses for at least 4 months prior to study entry. The dose of MTX was 12.5–25 mg/week (oral, subcutaneous or intramuscular) and remained constant throughout the study (Screening, Treatment and Follow-up Phases).

Patients were sequentially enrolled into the study in dose cohorts starting with the lowest dose of IL-10. Safety was assessed for each dose level prior to progressing to the next higher dose. Ten patients were assessed at each of the IL-10 dose cohorts: 8 received IL-10 and 2 received placebo (4:1). There was no replacement of patients.

The primary objective was to evaluate, in a dose-escalating manner, the safety and tolerance of IL-10 (SC) therapy given daily or TIW plus MTX (oral/intramuscular/SC) over a 28 day period to patients with active rheumatoid arthritis. The secondary objectives were to evaluate the effect of IL-10 on measures of rheumatoid arthritis Disease Activity, and to determine changes in the circulating levels of soluble p55 and p75 TNF receptors and IL-1 receptor antagonist. Protocol-defined responders were defined as those patients with at least 20% ACR criteria, i.e. at least 20% improvement in number of tender joints, number of swollen joints and in at least 3 of 5 RA Disease Activity measures (i.e. subject's assessment of pain, disease activity or physical function and physician's global assessment of disease activity.

Fifty patients were enrolled and sequentially randomized to receive one of the five dosing regimens of IL-10 (SC) (1 $\mu$g/kg daily, 4 $\mu$g/kg daily, 8 $\mu$g/kg TIW, 8 $\mu$g/kg daily and 20 $\mu$g/kg TIW) or placebo which formed the intent-to-treat population (ITT). Mean duration of treatment was at least 26 days for each of the treatment groups. The treatment groups were similar in demographic characteristics except for slight differences in age. Baseline characteristics of RA Disease Activity were similar for treatment groups.

IL-10 was generally well tolerated. No anti-dsDNA or anti IL-10 antibodies were present at any time during the study. The most frequently reported adverse events were headache, injection site reaction, nausea, musculoskeletal pain, with no dose-response relationship seen.

Protocol-defined response was evaluated after 28 days of dosing versus baseline for the ITT population. Results showed a trend toward a greater percentage of responders in patients treated with IL-10 compared with the placebo group. Similar trends were seen for mean change from baseline for individual clinical measures of rheumatoid arthritis disease activity, with IL-10 treatment groups generally showing a greater percentage of responders than in placebo group. The percent of patients having a 20% improvement in disease activity (ACR 20) and that of patients having a 50% improvement in disease activity (ACR 50) was higher for each of the IL-10 treatment groups than for the placebo group, with the higher dose groups (8 $\mu$g/kg TIW, 8 $\mu$g/kg daily and 20 $\mu$g/kg TIW) showing the highest percent of both 20 ACR and 50 ACR responders. A trend towards decreased production of ex-vivo induced proinflammatory cytokines (TNF$\alpha$ and IL-1$\beta$) and a trend towards increased circulating serum levels of soluble TNF p55 and TNF p75 receptors and IL-1 receptor antagonists occurred in nearly all IL-10 treatment groups compared with placebo.

The following conclusions can be drawn from this study. IL-10, in combination with stable dosing of MTX, was safe and well tolerated in patients with active rheumatoid arthritis. Trends indicate that IL-10 in combination with MTX may have beneficial effects on rheumatoid arthritis Disease Activity. This effect was greatest for the 8 $\mu$g/kg TIW, 8 $\mu$g/kg daily and 20 $\mu$g/kg TIW IL-10 dosing regimens. The dosing regimen which maximizes safety and efficacy results is 8 $\mu$g/kg IL-10 TIW.

Many modifications and variations of this invention can be made without departing from its spirit and scope, as will be apparent to those skilled in the art. The specific embodiments described herein are offered by way of example only, and the invention is to be limited by the terms of the appended claims, along with the full scope of equivalents to which such claims are entitled; and the invention is not to be limited by the specific embodiments that have been presented herein by way of example.

We claim:

1. A method of treating rheumatoid arthritis, said method comprising administering an effective amount of interleukin 10 and methotrexate to an individual afflicted with rheumatoid arthritis.

2. The method of claim 1 wherein the interleukin 10 is human interleukin 10.

3. The method of claim 1 wherein the interleukin 10 is viral interleukin 10.

4. A pharmaceutical composition comprising interleukin 10, methotrexate and a pharmaceutical acceptable carrier.

5. The composition of claim 4 wherein the interleukin 10 is human interleukin 10.

6. The composition of claim 4 wherein the interleukin 10 is viral interleukin 10.

* * * * *